(12) United States Patent
Burkett et al.

(10) Patent No.: US 6,241,690 B1
(45) Date of Patent: Jun. 5, 2001

(54) GUIDEWIRE HAVING EXCHANGEABLE INNER MEMBER

(75) Inventors: David H. Burkett; John S. Greenland, both of San Diego, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/084,606

(22) Filed: May 26, 1998

(51) Int. Cl.$^7$ .................................................. A61B 5/00
(52) U.S. Cl. ............................................ 600/585; 604/523
(58) Field of Search .................................... 600/585, 433, 600/434; 604/95, 96, 280, 281

(56) References Cited

U.S. PATENT DOCUMENTS

| | | | |
|---|---|---|---|
| 4,676,249 | 6/1987 | Arenas et al. | 128/657 |
| 4,873,983 | 10/1989 | Winters | 128/657 |
| 4,895,168 | 1/1990 | Machek | 128/772 |
| 5,040,543 | 8/1991 | Badera et al. | 128/772 |
| 5,184,627 | 2/1993 | de Toledo | 128/772 |
| 5,246,009 | 9/1993 | Adams | 128/772 |
| 5,303,714 | 4/1994 | Abele et al. | 128/772 |

FOREIGN PATENT DOCUMENTS

| | | |
|---|---|---|
| 41 30 042 A1 | 3/1993 | (DE). |
| 0 778 040 A2 | 6/1997 | (EP). |
| 0 823 261 A2 | 2/1998 | (EP). |

*Primary Examiner*—Max Hindenburg
*Assistant Examiner*—Pamela L. Wingood
(74) *Attorney, Agent, or Firm*—Heller, Ehrman, White & McAuliffe LLP

(57) ABSTRACT

A guidewire which has a tubular member, a flexible distal tip secured to the distal end of the tubular member and an exchangeable elongated core member disposed within the lumen of the tubular member. The elongated core member can be advanced distally to the distal end of the tubular member or withdrawn proximally out of the tubular member proximal end. While the guidewire is inside a patient's vessel, the elongated core member can be removed from the tubular member and exchanged for a different elongated support. By exchanging the elongated core member, the physician is able to change guidewire characteristics, such as flexibility or shape, to facilitate movement of the guidewire within the patient's lumen.

26 Claims, 1 Drawing Sheet

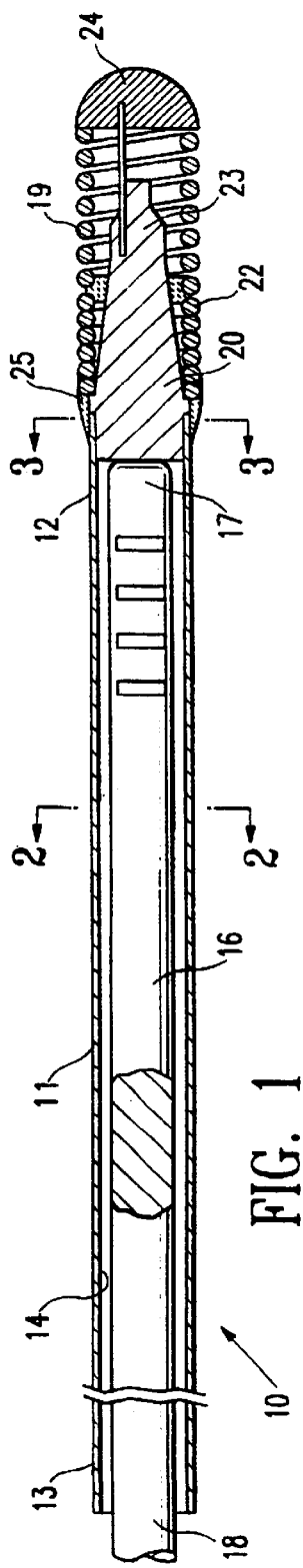
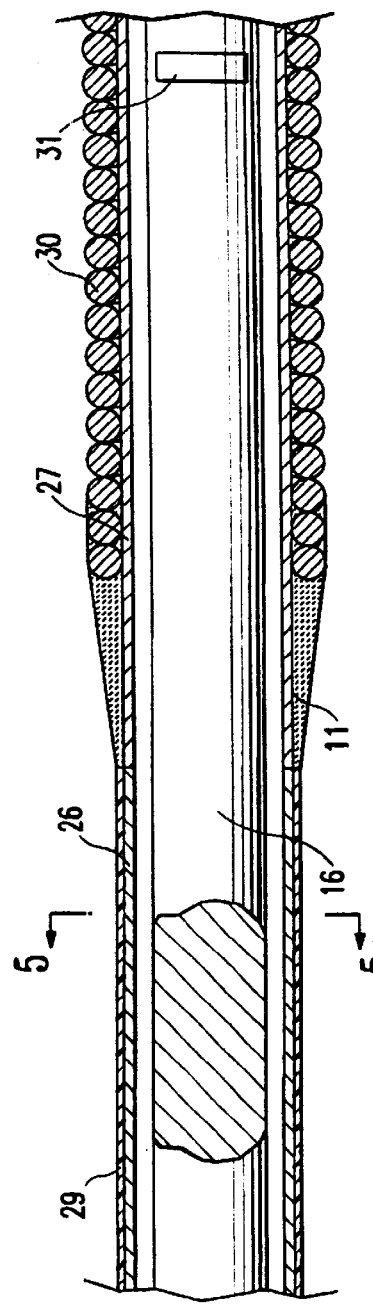

GUIDEWIRE HAVING EXCHANGEABLE INNER MEMBER

BACKGROUND OF THE INVENTION

This invention relates to the field of medical devices, and more particularly to a guidewire for advancing a catheter within a body lumen in a procedure such as percutaneous transluminal coronary angioplasty (PTCA).

Catheters are generally elongated tubular devices for performing a variety of functions, and include operative catheters, such as angioplasty catheters, and guiding catheters such as those used for the introduction of operative devices or fluids to various locations within a patient's body. Many catheters are generally too flexible to be advanced unassisted and therefore are used with a guiding means such as a guidewire. For example, in a typical PTCA procedure a guiding catheter having a preformed distal tip is percutaneously introduced into the cardiovascular system of a patient in a conventional Seldinger technique and advanced therein until the distal tip of the guiding catheter is seated in the ostium of a desired coronary artery. A guidewire is then advanced through the guiding catheter either by itself or together with a dilatation catheter having an inflatable balloon on the distal portion thereof. The guidewire is first advanced out of the distal end of the guiding catheter into the patient's coronary vasculature until the distal end of the guidewire crosses a lesion to be dilated, then the dilatation catheter is advanced into the patient's coronary anatomy until the balloon is properly positioned across the lesion. Once in position across the lesion, the balloon is inflated to dilate the stenosed region and open up the lumen of the artery. The dilatation catheter may then be removed following deflation of the balloon.

Conventional guidewires for angioplasty and other vascular procedures usually comprise an elongated core member with one or more tapered sections near the distal end thereof and a flexible body such as a helical coil disposed about the distal portion of the core member. The distal extremity of the guidewire usually is shapeable, so that when torque is applied to the proximal end of the guidewire outside of the patient as the guidewire is advanced there through, the shaped distal extremity can be steered through the patient's vascular system.

A major requirement for guidewires and other guiding members, whether solid wire or tubular members, is that they have sufficient strength to be pushed through a patient's vascular system or other body lumen, and be flexible enough to be maneuvered within the patient, without inflicting trauma to the patient's vessel or other body lumen through which they are advanced. At the same time, they must have sufficient structural integrity that portions of the guidewire do not break off while inside the patient. Efforts to produce a guidewire having optimum strength and flexibility have been hampered by the fact that the strength and flexibility requirements are diametrically opposed, in that an increase in one usually involves a decrease in the other.

Often while attempting to advance the guidewire though the patient's vasculature, the guidewire and catheter combination will prove to have insufficient strength or flexibility to be fully advanced. For example, a relatively flexible guidewire is best suited for the initial advancement within the vessel, while a guidewire with less flexibility is needed to continue advancement once the guidewire is deep within the patient. Therefore, it can become necessary for the physician to exchange the guidewire to complete the advancement. However, in order to exchange a guidewire, the access achieved by the guidewire within the patient's vasculature must be sacrificed, and the time consuming process of advancing a replacement guidewire must be performed. In addition to increasing the duration of the procedure, the exchange increases the risk of trauma to the patient's vasculature from guidewire impact on the vessel wall.

Attempts to produce guidewires that are adaptable to different situations inside the patient's lumen, which thereby avoid exchange of the guidewire after introduction into the patient, include guidewires made of pseudoelastic or shape memory material and moveable core guidewires. Moveable core guidewires generally have a solid inner core that can be moved in and out of a flexible distal end coil, to thereby change the flexibility of the distal end of the guidewire. It has been found that because the solid core is generally significantly less flexible than the distal end, the core is prone to piercing through the flexible distal end coil during advancement of the solid core. Guidewires made from pseudoelastic and/or shape memory materials such as NITINOL (NiTi alloy) generally have a tensile strength and/or shape which can be changed in response to a change in restraining force or temperature while the guidewire is inside the body. For example, pseudoelastic, shape memory alloys generally have at least two phases, a martensite phase, which has a relatively low tensile strength and which is stable at relatively low temperatures, and an austenite phase, which has a relatively high tensile strength and which is stable at temperatures higher than the martensite phase. A switch from one phase to the other will change the strength and possibly the shape of the material. While inside the patient, a guidewire made from these alloys may undergo one permanent phase change with a corresponding change in strength or shape, or may possibly cycle between two phases. However, like the moveable core guidewire, pseudoelastic shape memory alloy guidewires provide only limited procedural flexibility to the physician, in that guidewires produced using such techniques possess only one or two strength or shape options that the physician may change between during use.

Attempts at producing one guidewire with optimum strength and flexibility for the multitude of situations encountered within a patient's lumen have proven unsuccessful. What has been needed is a guidewire which is easily adaptable to any situation within a patient's lumen, to provide procedural flexibility while minimizing cost and procedural complexity.

SUMMARY OF THE INVENTION

The present invention is directed to a guidewire which has a tubular member, a flexible distal tip secured to the distal end of the tubular member, and an exchangeable elongated core member disposed within the lumen of the tubular member. The elongated core member can be advanced distally to the distal end of the tubular member or withdrawn proximally out of the tubular member proximal end. The elongated core member does not affect the flexible distal tip, in that the distal extremity of the elongated core member is located proximally to the proximal end of the flexible distal tip. While the guidewire is inside a patient's lumen, such as a blood vessel, the elongated core member can be removed from the tubular member and exchanged for a different elongated core member which provides the desired characteristics. Thus, by exchanging the elongated core member, the physician is able to change guidewire characteristics, such as flexibility or shape, to facilitate movement of the guidewire within the patient's lumen or to provide additional stiffness if additional guidewire support is needed to advance an intraluminal device over the guidewire.

The guidewire of the invention allows for the creation of a tubular member and elongated core member combination that can be adapted to a wide variety of situations encountered while advancing the guidewire within the patient's lumen. The tubular member is configured to be both flexible and strong. In general, the tubular member is a thin walled strong material, such as a superelastic, or pseudoelastic material, or a material with shape memory at body temperature. The presently preferred material is NITINOL (NiTi) hypotube due to its flexibility, memory, strength and torqueability. The elongated core member may be configured in any number of ways to provide a range of desired characteristics. For example, the elongated core member may be made from a variety of materials and with shaped or shapeable portions, to provide the physician with a multitude of options when using the guidewire. Moreover, the guidewire of the invention is provided in various sizes with different diameters and lengths to suit different clinical needs.

A method of using the guidewire assembly of the invention within a patient's lumen comprises providing a guidewire of the invention having a tubular member and an exchangeable elongated core member disposed therein. The guidewire is advanced in the patient until different flexibility and shape or support characteristic is desired. At that point, the elongated core member is withdrawn proximally out the tubular member proximal end, and another exchangeable elongated core member having different characteristics is advanced distally within the tubular member lumen. The elongated core member can be exchanged for another elongated core member in this manner any number of times, while the tubular member is left in place inside the patient's lumen to act as a guide for the elongated core member and to protect the patient's lumen.

Because the tubular member can remain in place inside the patient throughout the surgical procedure, the access achieved by a guidewire which has been partially advanced within the patient is not lost when a exchangeable elongated core member is exchanged to modify the guidewire characteristics.

The tubular member may be used alone without an elongated core member to provide a more flexible guidewire, either from the initial introduction into the patient or after a different flexibility or shape characteristic is needed or desired during the advancement. The tubular member would be used alone until additional strength is desired, at which point an elongated core member is disposed in the tubular member lumen to provide the needed strength.

The preferred guidewire of the invention is provided with a flexible distal tip which is shapeable to facilitate maneuverability of the guidewire within the patient's body lumen. Because the exchangeable elongated core member is not advanceable into or around the shapeable, flexible distal tip, the distal tip provides guidewire steerability independent of the exchangeable elongated core member.

The use of the guidewire of the invention having an exchangeable elongated core member provides the physician with excellent procedural flexibility. By using the tubular member alone or with different elongated core members having different flexibility or shapes, the guidewire is adaptable to suit a wide variety of situations encountered during the procedure, without requiring an exchange of the entire guidewire unit. The physician is able to use a single guidewire which can be provided with a variety of characteristics during a procedure without the need to withdraw the guidewire from the patient. Moreover, the stiffness can be varied throughout the procedure quickly and without risk of trauma to the patient's lumen because the tubular member remains within the lumen to act as a guide for the elongated core members being exchanged. Additionally, because the elongated core member never comes into contact with the patient's bloodstream or tissue, the risk of infections is lower than that created by the exchange of conventional guidewires. Similarly, the elongated core member may be formed from materials which might not be acceptable for direct contact with the patient's blood and tissue. These and other advantages of the invention will become more apparent from the following detailed description thereof when taken in conjunction with the following exemplary drawings.

BRIEF DESCRIPTION OF THE DRAWINGS

FIG. 1 is longitudinal cross sectional view of a guidewire which embodies features of the invention.

FIG. 2 is a transverse cross sectional view of the guidewire shown in FIG. 1, taken along lines 2—2.

FIG. 3 is a transverse cross sectional view of the guidewire shown in FIG. 1, taken along lines 3—3.

FIG. 4 is a partial longitudinal cross sectional view of a guidewire which embodies features of the invention.

FIG. 5 is a transverse cross sectional view of the guidewire shown in FIG. 4, taken along lines 5—5.

DETAILED DESCRIPTION OF THE INVENTION

FIG. 1 illustrates a guidewire 10 embodying features of the invention that is adapted to be advanced in a patient's body lumen, such as a blood vessel. The guidewire 10 comprises a tubular member 11 having a distal end 12, a proximal end 13, a lumen 14 extending therein, and an exchangeable elongated core member 16 having distal 17 and proximal 18 ends. The exchangeable elongated core member 16 is slidably disposed within the tubular member lumen 14. The exchangeable elongated core member 16 may be distally advanced to the tubular member distal end 12, and proximally withdrawn out of the tubular member proximal end 13, so that the exchangeable elongated core member is configured to be removable from the tubular member lumen 14, and exchangeable for a different elongated core member (not shown). The guidewire is provided with a flexible distal tip 19 having a proximal end 20 secured to the distal end 12 of the tubular member 11, and configured to facilitate maneuverability of the guidewire 10. As illustrated in FIG. 1, the exchangeable elongated core member 16 is advanceable only to a point located proximal to the proximal end 20 of the flexible distal tip 19, and cannot be advanced into or around the flexible distal tip 19.

The guidewire 10 of the invention is configured so that the physician can combine different elongated core members 16 with a tubular member 11 inside a patient's lumen. While moving the guidewire 10 within a patient, a tubular member 11 and elongated core member 16 combination can be created that facilitates that movement by being ideally suited for the conditions encountered within the patient's lumen. The different exchangeable elongated core members 16 can be formed from a variety of materials having different flexibility, strength, and memory characteristics. The presently preferred exchangeable elongated core member material is selected from the group consisting of a NiTi alloy, stainless steel, hardened steel, and titanium. However, it would be obvious to one skilled in the art that a variety of suitable materials exist that would provide exchangeable elongated core members 16 having characteristics desirable for facilitating movement of the guidewire 10 within a patient's lumen.

The guidewire of the invention is provided with a flexible distal tip 19 having a proximal end 20 secured to the distal end of the tubular member 11. A presently preferred embodiment of a flexible distal tip is illustrated in FIG. 1, and comprises helical coils 22, a core member 23 therein, and a nontraumatic distal tip 24. The flexible distal tip 19 is generally secured to the tubular member 11 via a silver/tin solder connection 25, although the connection can be made by a variety of suitable methods including welding, brazing, and use of adhesive. FIG. 3 illustrates a cross sectional view of the flexible distal tip 19 secured to the tubular member 11. The flexible distal tip 19 may be shaped or shapeable to facilitate maneuverability of the guidewire within the patient's body lumen.

The tubular member 11 is configured to be useable with or without an elongated core member 16 within the tubular member lumen 14. The ends of the tubular member 11 may have external tapering to provide flexibility, and the core member distal end 18 may be tapered to facilitate movement within the tubular member 11. In a presently preferred embodiment, the tubular member 11 is formed from stainless steel or from a pseudoelastic shape memory alloy such as a NiTi alloy. FIG. 4 illustrates another embodiment of the invention, in which the tubular member 11 comprises a proximal portion 26, and a distal portion 27 having a flexibility that is greater than that of the proximal portion 26. The presently preferred material of the tubular member proximal portion 26 is stainless steel, while that of the distal portion 27 is a NiTi alloy.

The tubular member 11 is preferably provided with a coating of lubricious material such as TEFLON or a hydrophilic polymer, to reduce friction. As illustrated in FIG. 4, in a presently preferred embodiment, a friction reducing coating 29 and radiopaque helical coils 30 are disposed about the tubular member 11. In the embodiment illustrated in FIG. 4, the coating 29 is on the proximal portion 26 of the tubular member 11, and the helical coil 30 is disposed about the distal portion 27 of the tubular member 11. FIG. 5 illustrates a transverse cross section of the guidewire shown in FIG. 4, illustrating the proximal portion 26 of the tubular member 11. Radiopaque marking bands 31 may be applied to the exchangeable elongated core member 16 or tubular member 11 to facilitate location of the guidewire 10 within the body and the measurement of lesion dimensions. The guidewire 10 provides improved measuring and imaging of the lesion site. The marking bands 31 on the core member 16 can be positioned without displacing the tubular member 11. Consequently, with the guidewire in place across the lesion, the physician can measure the lesion size and then move the markers out of the way during fluoroscopy by displacing the core member 16, to provide a clearer view of the lesion and the effect of the intervention.

The tubular member 11 outer diameter is typically about 0.02 to about 0.075 cm (0.008 to about 0.03 in.), preferably about 0.025 to about 0.055 cm (0.010 to about 0.022 in). The presently preferred outer diameter is 0.035 cm (0.014 in). The wall thickness of the tubular member 11 is typically about 0.0013 to about 0.007 cm (0.0005 to about 0.0028 in), preferably about 0.0025 to about 0.005 cm (0.001 to about 0.002 in). The presently preferred tubular member wall thickness is 0.0038 cm (0.0015 in).

In operation of the assembly, the guidewire 10 having an exchangeable elongated core member 16 positioned within a tubular member 11, is inserted into the patient's lumen and advanced therein. While advancing the guidewire 10, if the guidewire flexibility or shape characteristics are not adequate for further advancement, the first exchangeable elongated core member 16 is withdrawn out the proximal end 13 of the tubular member 11. At that point the tubular member 11 remaining inside the patient can be advanced alone, or a different exchangeable elongated core member 16 can be advanced distally within the tubular member lumen 14 to form a second guidewire. This procedure of removing and exchanging the elongated core members 16 while the tubular member remains inside the patient's lumen can be repeated as often as necessary to advance the guidewire 10 to the desired location within the lumen. The removal or exchange of the elongated core member 16 facilitates the advancement or retraction of the guidewire within the patient, or the crossing of an occlusion in a vessel. Additionally, as mentioned above, the physician could begin a procedure requiring a particularly flexible guidewire by using a tubular member 11 alone, and only later adding an exchangeable elongated core member 16 as needed for additional strength.

In one aspect of the invention, the exchangeable elongated core member 16 has a longitudinal length greater than that of the tubular member to facilitate removal of the exchangeable elongated core member 16 from the tubular member 11. In this aspect, the proximal end 18 of the exchangeable elongated core member 16 extends proximally of the tubular member proximal end 13. In a presently preferred embodiment, with the exchangeable elongated core member 16 fully disposed within the tubular member, the core member proximal end extends proximally about 2 cm to about 50 cm from the tubular member proximal end, and most preferably about 5 cm to about 10 cm from the tubular member proximal end. However, the length of the exchangeable core member 16 will depend upon the desired guidewire length and the length of the distal tip section of the tubular member. Typical lengths of convention guidewires are about 190 cm to about 300 cm. The exchangeable elongated core member has a length of about 185 cm to about 350 cm, and the tubular member has a length of about 180 cm to about 300 cm.

During advancement of the guidewire 10, the exchangeable elongated core member 16 distal end 17 can be positioned at the distal end of the tubular member 11 to create a guidewire of uniform flexibility throughout its length, or it may be positioned proximal to the tubular member distal end to increase the flexibility of the distal end of the guidewire 10. In either case, the exchangeable the distal end 17 of the elongated core member 16 is located proximally to the proximal end 20 of the flexible distal tip 19. Also, removal or exchange of the exchangeable elongated core member 16 obviously changes the guidewire characteristics along the entire length of the guidewire 10.

While the invention has been described in terms of certain preferred embodiments, it will be obvious to one skilled in the art that various modifications and improvements could be made to the invention without departing from the scope thereof.

What is claimed is:

1. A guidewire, comprising:
   a) a tubular member having a distal end and a proximal end, and a lumen extending therein;
   b) an exchangeable elongated core member having a proximal end and a distal end, and being slidably disposed within the lumen of the tubular member, and c) a flexible distal section having a distal end and a proximal end, with the proximal end of the distal section being secured to the distal end of the tubular member at a junction which precludes passage of the distal end of the exchangeable elongated core member.

2. The guidewire of claim 1 wherein the proximal end of the exchangeable elongated core member is located proximally of the proximal end of the tubular member.

3. The guidewire of claim 1 wherein the distal end of the exchangeable elongated core member is located proximally of the proximal end of the flexible distal tip.

4. The guidewire of claim 1 wherein the flexible distal tip is shapeable.

5. The guidewire of claim 1 wherein the tubular member outer diameter is about 0.02 cm to about 0.075 cm.

6. The guidewire of claim 1 wherein the tubular member outer diameter is about 0.035 cm.

7. The guidewire of claim 1 wherein the tubular member wall thickness is about 0.0013 cm to about 0.007 cm.

8. The guidewire of claim 1 wherein the tubular member wall thickness is about 0.0038 cm.

9. The guidewire of claim 1 wherein the exchangeable elongated core member has a length of about 185 cm to about 350 cm.

10. The guidewire of claim 1 wherein the tubular member has a length of about 180 cm to about 300 cm.

11. The guidewire of claim 1 wherein the exchangeable elongated core member is formed from a material selected from the group consisting of NiTi alloy, stainless steel, hardened steel, and titanium.

12. The guidewire of claim 1 wherein the tubular member is formed of a material selected from the group consisting of NiTi alloy and stainless steel.

13. The guidewire of claim 1 wherein the tubular member comprises a proximal portion, and a distal portion, with the distal portion having greater flexibility than the proximal portion.

14. The guidewire of claim 13 wherein the tubular member proximal portion is formed of stainless steel and the distal portion is formed of NiTi alloy.

15. The guidewire of claim 1 including at least one radiopaque marker on the elongated core member.

16. A method of using a guidewire assembly within a patient's body lumen, comprising:
   a) providing a guidewire comprising:
      a tubular member having a distal end and a proximal end, and a lumen extending therein;
      an exchangeable elongated core member having a proximal end and a distal end, and being slidably disposed within the lumen of the tubular member; and
      a flexible distal tip secured to the distal end of the tubular member;
   b) advancing the guidewire in the patient's body lumen; and
   c) withdrawing the elongated core member proximally out the proximal end of the tubular member.

17. The method of claim 16 further including, after step (c), advancing another elongated core member distally in the tubular member lumen within the patient's lumen.

18. The method of claim 16 wherein the elongated core member includes at least one radiopaque marker and including, after step (b), the step of positioning the radiopaque marker at a desired site in the patient's lumen.

19. The method of claim 18 including the steps of displacing the radiopaque marker from the desired site, and fluoroscopically imaging the site.

20. The guidewire of claim 1 wherein the flexible distal section has a core element which is secured to the distal end of the tubular member.

21. The guidewire of claim 20 wherein the flexible distal section has a flexible body disposed about at least part of the core element.

22. The guidewire of claim 21 wherein the flexible body is at least in part a helical coil.

23. The guidewire of claim 21 wherein a shapeable element extends from the core element to a distal end of the flexible body.

24. The guidewire of claim 23 wherein the shapeable element is in the form of a ribbon.

25. The guidewire of claim 1 wherein the distal end of the tubular member is closed by the proximal end of the flexible distal section which prevents passage of exchangeable core member beyond the distal end of the tubular member.

26. A guidewire, comprising:
   a) a tubular member having a distal end and a proximal end, and a lumen extending therein;
   b) an exchangeable elongated core member having a proximal end and a distal end, and being slidably disposed within the lumen of the tubular member;
   c) a flexible distal section having a distal end and a proximal end, with the proximal end of the distal section being secured to the distal end of the tubular member; and
   d) means for precluding passage of the distal end of the exchangeable elongated core member beyond the distal end of the tubular member.

* * * * *